United States Patent
Meyer et al.

(10) Patent No.: US 11,633,295 B2
(45) Date of Patent: Apr. 25, 2023

(54) METHOD FOR ADAPTING THE HEEL HEIGHT OF A PROSTHETIC FOOT

(71) Applicant: OTTOBOCK SE & CO. KGAA, Duderstadt (DE)

(72) Inventors: Hermann Meyer, Gottingen (DE); Sven Kaltenborn, Duderstadt (DE); Steffen Althaus, Breitenworbis (DE)

(73) Assignee: OTTOBOCK SE & CO. KGAA, Duderstadt (DE)

( * ) Notice: Subject to any disclaimer, the term of this patent is extended or adjusted under 35 U.S.C. 154(b) by 322 days.

(21) Appl. No.: 16/783,556

(22) Filed: Feb. 6, 2020

(65) Prior Publication Data

US 2020/0170808 A1 Jun. 4, 2020

Related U.S. Application Data

(62) Division of application No. 15/319,337, filed as application No. PCT/EP2015/067065 on Jul. 24, 2015, now Pat. No. 10,588,760.

(30) Foreign Application Priority Data

Jul. 28, 2014 (DE) .......................... 102014010938.0

(51) Int. Cl.
*A61F 2/66* (2006.01)
*A61F 2/70* (2006.01)
(Continued)

(52) U.S. Cl.
CPC .............. *A61F 2/6607* (2013.01); *A61F 2/70* (2013.01); *A61F 2002/5001* (2013.01); *A61F 2002/5018* (2013.01); *A61F 2002/6614* (2013.01); *A61F 2002/6642* (2013.01); *A61F 2002/6664* (2013.01); *A61F 2002/6809* (2013.01);
(Continued)

(58) Field of Classification Search
CPC .. A61F 2/66; A61F 2/6607; A61F 2002/5061; A61F 2002/5058; A61F 2002/6607; A61F 2002/6609; A61F 2002/6827; A61F 2002/689; A61F 2002/6854; A61F 2002/7615; A43B 3/24
See application file for complete search history.

(56) References Cited

U.S. PATENT DOCUMENTS 7,520,904 B2 4/2009 Christensen
8,246,695 B2 8/2012 Mosler
(Continued)

FOREIGN PATENT DOCUMENTS

CN 1514703 7/2004
CN 1964682 5/2007
(Continued)

OTHER PUBLICATIONS

PCT International Search Report for PCT International Patent Application No. PCT/EP2015/067065, dated Nov. 12, 2015.

*Primary Examiner* — Christie L Bahena
(74) *Attorney, Agent, or Firm* — Holland & Hart LLP

(57) ABSTRACT

A prosthetic foot comprising a foot part, a proximal connecting member which is swiveled to the foot part and an adjustment device with which the foot part can be adjusted relative to the connecting member, and at least one position sensor being associated with the adjustment device and being coupled to a signal generating element.

19 Claims, 12 Drawing Sheets

(51) Int. Cl.
*A61F 2/50* (2006.01)
*A61F 2/68* (2006.01)
*A61F 2/76* (2006.01)

(52) U.S. Cl.
CPC . *A61F 2002/689* (2013.01); *A61F 2002/6827* (2013.01); *A61F 2002/6881* (2013.01); *A61F 2002/7625* (2013.01)

(56) References Cited

U.S. PATENT DOCUMENTS

| | | | |
|---|---|---|---|
| 8,751,320 | B1 | 6/2014 | Kemist |
| 8,945,238 | B2 | 2/2015 | Mosler et al. |
| 9,844,448 | B2 | 12/2017 | Karlsson et al. |
| 2002/0143406 | A1 | 10/2002 | Townshend et al. |
| 2004/0186592 | A1 | 9/2004 | Townshend et al. |
| 2005/0197717 | A1 | 9/2005 | Ragnarsdottir et al. |
| 2006/0041321 | A1 | 2/2006 | Christensen |
| 2006/0173552 | A1 | 8/2006 | Roy |
| 2006/0224246 | A1 | 10/2006 | Clausen et al. |
| 2006/0282174 | A1 | 12/2006 | Haines |
| 2007/0050045 | A1 | 3/2007 | Clausen et al. |
| 2009/0222105 | A1 | 9/2009 | Clausen |
| 2011/0230975 | A1 | 9/2011 | Moser et al. |
| 2013/0024007 | A1 | 1/2013 | Kaltenborn et al. |
| 2013/0190896 | A1 | 7/2013 | Brocki et al. |
| 2014/0371871 | A1 | 12/2014 | Farina et al. |
| 2015/0157087 | A1* | 6/2015 | Blumenthal ............. A43B 3/24 36/100 |
| 2015/0257902 | A1 | 9/2015 | Martin |

FOREIGN PATENT DOCUMENTS

| | | |
|---|---|---|
| CN | 101151071 A | 3/2008 |
| CN | 101437470 | 5/2009 |
| CN | 102036626 | 4/2011 |
| CN | 201160923 | 12/2018 |
| DE | 60309685 T2 | 9/2007 |
| DE | 112005002613 T5 | 9/2007 |
| EP | 2340789 B1 | 7/2011 |
| EP | 2564817 B1 | 3/2013 |
| EP | 2649968 A2 | 10/2013 |
| JP | 63-69655 | 5/1988 |
| JP | 2004-33693 | 2/2004 |
| JP | 2004033693 A | 2/2004 |
| JP | 2008104737 A | 5/2008 |
| RU | 2352297 C2 | 4/2009 |
| RU | 2419398 C2 | 5/2011 |

* cited by examiner

Assigning a heel height marking to the shoe, the heel height marking represents a heel height of the shoe.

Assigning a position signal to the heel height marking.

Transmitting a value of the heel height marking to the control device.

Adjusting the heel height at least partially based on the heel height marking.

Comparing, with the control device, the value of the heel height marking with detected position data from the at least one position sensor.

Emitting a confirmation signal with the output device when the position signal assigned to the heel height marking matches with the detected position data.

FIG. 12

METHOD FOR ADAPTING THE HEEL HEIGHT OF A PROSTHETIC FOOT

CROSS REFERENCE TO RELATED APPLICATION

This application is a divisional of U.S. patent application Ser. No. 15/319,337, filed 15 Dec. 2016, and entitled PROSTHETIC FOOT, SYSTEM OF A PROSTHETIC FOOT AND A SHOE, AND METHOD FOR ADAPTING THE HEEL HEIGHT OF A PROSTHETIC FOOT, which is a U.S. national entry application from PCT International Patent Application No. PCT/EP2015/067065, filed Jul. 24, 2015, and also entitled PROSTHETIC FOOT, SYSTEM OF A PROSTHETIC FOOT AND A SHOE, AND METHOD FOR ADAPTING THE HEEL HEIGHT OF A PROSTHETIC FOOT, which claimed the benefit of German Patent Application No. 102014010938.0, filed 28 Jul. 2014, the disclosures of which are incorporated, in their entireties, by this reference.

TECHNICAL FIELD

The invention relates to a prosthetic foot having a foot part, a proximal connection means which is connected tiltably to the foot part, and an adjustment device with which the foot part can be adjusted relative to the connection means. The invention furthermore relates to a system consisting of such a prosthetic foot and a shoe, as well as to a method for adapting the heel height of a prosthetic foot to a shoe, which is assigned a heel height marking.

BACKGROUND

In the prosthetic treatment of lower extremities, it is necessary to provide a set-up adapted to the patient. A set-up is intended to mean the assignment and alignment of all prosthetic components with respect to one another. In the case of patients having a prosthetic knee joint, it is necessary to adjust the orientation and positioning of the prosthetic knee joint and of its rotation axis precisely, and to select and mount the length of the lower limb tube as well as the suitable prosthetic foot. Depending on the patient, it is possible to select a dynamic or secure set-up. In the standing phase, the further the resultant force vector lies in front of the knee axis, the more secure the set-up is, and the closer the resultant force vector is shifted toward the rotation axis of the knee joint prosthesis, the more dynamic the set-up is. If the set-up is secure, the risk of unintended flexion of the prosthetic knee joint is reduced, although relatively high expenditure of energy is necessary when walking. A dynamic set-up makes it easier to flex the prosthetic knee joint in the standing phase both during the heel strike and at the end of the standing phase, as well as in the swing phase. For walking, the user requires comparatively less exertion of force, but the prosthetic knee joint is susceptible to flexion more easily, which may be undesired in some situations.

Besides the set-up of the prosthetic knee joint, the prosthetic foot plays a role which should not be underestimated, since the contact with the ground is established via the prosthetic foot. The prosthetic foot may have a very wide variety of configurations, there being manifold possibilities from a simple wooden block with a plastic shell to a hydraulically controlled, driven prosthetic foot. Conventional prosthetic feet may be worn in shoes, and therefore have an outer appearance approximating that of a normal foot shape. Sports feet are generally not worn in shoes. One problem for users of prostheses of lower extremities is that, when changing shoes, it is necessary to adapt the prosthetic foot to a different heel height compared with standard setting or the original setting. An orthopedic technician has to date adjusted the optimal set-up of a prosthesis for a standard heel height value, but if another heel height is selected for another shoe or a different shoe model, for example with a different heel drop or a different heel height is used it may be necessary to modify the inclination of the prosthetic foot relative to the lower limb tube, in order to carry out heel height adaptation. Otherwise, the entire set-up of the prosthesis is modified. A heel height adjustment may also be necessary when geometrically identical shoes are used. Because of different sole stiffnesses, it may be necessary for a different heel height to be adjusted. A softer heel may require a different heel height than a harder heel.

From the prior art, prosthetic feet are known which have a hydraulic adjustment device, so that an orthopedic technician can carry out an adaptation of the prosthetic foot to modified heel heights. A disadvantage with these solutions is that the orthopedic technician in principle needs to be consulted for each shoe change, with the aim of ensuring a statically and dynamically correct set-up. Furthermore, reproducibility of the adjustment results is not guaranteed.

A prosthetic foot is available under the name "Runway" from the company Freedom Innovations. The adjustment is carried out optionally by means of push-button adjustment or with a hex key.

The company Streifeneder sells a prosthetic foot insert with integrated heel height adjustment under the name "Accent", with which height adjustment of up to 51 mm can be achieved.

SUMMARY

It is an object of the present invention to provide a prosthetic foot, a system consisting of a prosthetic foot and a shoe, and a method for adapting a heel height of a prosthetic foot to a shoe, with which a prosthetic foot user can adapt the prosthetic foot to the respective shoe, the intention is for the adjustment to be carried out reproducibly so as to maintain the optimized prosthetic set-up.

According to the invention, this object is achieved by a prosthetic foot having the features of the present disclosure, by system consisting of a prosthetic foot and a shoe having the features of the present disclosure, as well as such a method with features of the present disclosure. Advantageous configurations and refinements of the invention are disclosed in the description and the figures. With the invention, it is possible to provide an improved prosthetic treatment. For patients with transtibial amputation, incorrect heel height adjustments lead to damage to capsules and ligaments both of the treated and of the untreated leg, while in the case of transfemoral amputations a nonoptimized heel height adjustment and modification of the prosthetic set-up lead to strains in the capsule and ligament apparatus of the knee of the untreated leg and to overloads of individual muscles. With the invention, these disadvantages are reduced or prevented.

In the prosthetic foot according to the invention having a foot part, a proximal connection means which is connected tiltably to the foot part, and an adjustment device with which the foot part can be adjusted relative to the connection means, the adjustment device is assigned at least one position sensor, which is coupled to a signal generating element. In order to adjust the heel height, it is necessary to modify the inclination of the foot part relative to the connection means starting from a heel height adjusted by the orthopedic technician, the prosthetic set-up is optimized by the orthopedic technician. If, starting from an initial setting, in the event of a modified heel height the foot part is flexed in the plantar direction, i.e. the tip of the foot is tilted in the direction of the floor so that the heel is raised relative thereto, the position sensor detects the angular position of the foot part relative to the proximal connection means, with which the prosthetic foot is fastened to the lower limb tube. The signal generating element may be configured as an active signal generating element and, as a function of the signal which is transmitted from the position sensor to the signal generating element, for example after evaluation in a control unit, emit an optical, acoustic or tactile signal so that the prosthesis user knows the level which the heel height adjustment is currently occupying. The output may be carried out acoustically, for example by voice output with which the respectively reached heel height level is indicated. It is likewise possible that a signal tone is output after the next respective heel height level is reached, in which case different signal tones may be assigned to the respective heel height levels. It is also possible for different tone levels, signal patterns or signal sequences to be assigned to the respective heel level. If there are six heel height levels, for example, each may be characterized with a corresponding number of tones, the third level with three successive signal tones, the fourth level with four, and so on. Besides acoustic signal output, it is possible to provide tactile signal output, for example by vibrations, vibration patterns or the like. Furthermore, as an alternative or in addition, it is possible to output an optical signal, for example a light signal, light signal pattern or optionally a display of the current heel height level. As an alternative or cumulatively, all signals may be used for each level. It is also possible to output different signal types for different heel height levels, and for example particular heel height levels may be indicated only acoustically, others only optically or in turn others only haptically. An optical display may, for example, also be carried out by means of different color signals. Because of the signal output, it is no longer necessary to consult the orthopedic technician for each heel height modification; rather, for different heel heights, it is sufficient to assign the respective heel height levels to the signals so that, after first adjustment of the prosthetic set-up and optionally assignment of different heels with different heel heights to the respective signals, with knowledge of the respective heel height of the shoe model in question the patient can independently carry out adaptation of the prosthetic foot to the respective heel height. Besides the active signal output elements or output devices described, it is possible and provided for passive signal generating elements to be provided, which do not require a separate energy source for the signal generation. For example, by means of a latching during the adjustment, a tactile signal may be output by means of so-called chatter marks, so that the prosthesis user or orthopedic technician knows by how many latch steps or heel height adjustment levels the foot part has been tilted relative to the connection means. Besides a passive and tactile output device, which also has an acoustic component, it is also possible for there to be an optical display of the heel height adjustment, for example by means of a color marking in a viewing window, or the display of a particular latch level by alphanumeric figures or other symbols.

The assignment of the signals, as well as the respective heel height adjustment, may also be carried out chronologically. The orthopedic technician and/or the patient may use any desired heel height in order to adjust the prosthetic set-up correctly. This heel height is then assigned a corresponding signal as a function of the time of the adjustment. If it is the first heel height adjusted, for example, a one-off signal tone or a one-off light signal or a one-off tactile signal takes place. A second heel height, which is different to the first heel height, chronologically receives a second signal, for example two signal tones, light signals or tactile signal outputs. The third storage of a heel height receives a third signal, etc., it being possible for the heel heights to be arbitrary, and the first heel height may represent a central heel, the second storage a high heel and the third a very flat heel.

The output of the heel height signal by the signal generating element may be carried out absolutely, so that the position respectively occupied is reported independently of an initial position. As an alternative thereto, the signal output may always be carried out starting from a standard initial position so that, for example, after the activation of an adjustment mode, only the number of heel height adjustment levels just carried out is respectively indicated.

The adjustment device may comprise latch elements, by means of which the adjustment of the foot part relative to the connection means takes place in discrete steps. The latching is to be selected sufficiently finely so that the most precise possible adjustment to the respective heel heights can be carried out, although on the other hand the latching should be selected coarsely enough so as not to output too many signals, which could cause confusion during the adjustment. It has been found sufficient that from 16 to 20 heel height steps are sufficient for effective heel height modification between 0 cm and 5 cm for sufficiently fine heel height adjustment with conventional shoe models.

The position sensor may be configured as a location sensor, relative angle sensor, inertial angle sensor, mechanical sensor and/or switch. In the case of a relative angle sensor, the relative position between the connection means and the foot part is detected, for example by means of magnets arranged in discrete steps, by means of induction, a Hall sensor or the like. It is likewise possible to arrange, at discrete angular intervals from one another, different markers which are detected by a detector and by which a corresponding signal is sent either directly to the signal generating element or to a control device. In contrast thereto, it is possible to provide a location sensor or inertial angle sensor on the foot part by means of which the absolute position of the foot part relative to a stationary reference quantity, generally the direction of gravity, is determined. After one-off alignment of the foot part, for example in a position without a shoe, by the modification of the location of the foot part relative to the direction of gravity in an adjustment mode it is possible to establish by how many degrees an adjustment takes place in the plantar flexion direction, from which in combination with the prosthetic foot length it is then possible to calculate the foot part position in which a particular heel height step is reached. The adjustment of the heel height is generally carried out under load, that is to say the patient stands uniformly loaded with an orthopedic technician. This means that in general 50% of the body weight is carried on the treated leg and 50% on the untreated leg. The storage of the respective heel height adjustment for the shoe or shoe model in question is carried out after static and dynamic adaptation of the prosthetic set-up by the orthopedic technician. The inertial angle sensor may be configured as a gyroscope. It is also possible for the position sensor to be configured as a simple switch, which is moved by a mechanical actuation element so that a circuit is opened or broken. Depending on the opening or closure of the circuit, a corresponding signal is output. Such switches may also be activated separately in order to achieve individual gradation, in a similar way to a mechanical timer switch with manually activatable switching times. According to the configuration as a mechanical sensor, the position sensor can function without electrical or electronic components, for example by an optical display or an acoustic signal being generated or modified in a purely mechanical way. The functionality in this case corresponds to that of a switch, but without the closure or opening of a contact.

The sensor device may be assigned an adjustable or programmable signal generator, so that both the intervals between the signals output and the nature of the respective signal can be established. It is also possible for a signal to be output when and only when the desired adjustment has been carried out. If a particular heel height is detected or adjusted, for example, it is possible to define by means of a confirmation device that a signal is output only when the respectively adjusted heel height position is reached. In this way, by means of automatic heel height detection, it is also possible to carry out simple adaptation of the orientation of the foot part relative to the proximal connection means, as it is only necessary to consider the presence or absence of a signal. Once the correct setting is reached, the signal is output, or conversely interrupted. For the prosthesis user, this is an indication to stop the adjustment and fix the position found.

The adjustment device may be assigned at least one receiver or a detector of shoe identification data, so that it is possible to detect automatically which shoe model or which heel height is arranged on the respective prosthetic foot. By means of the receiver or the detector, the prosthetic foot detects the shoe in which it has been placed, so that automatic adaptation of the signal generator or a control device takes place, so that simplified adaptation can be carried out on the basis of the automatic detection of the respective heel height. By the detector, for example, it is possible to detect automatically what the heel height is, so that by means of the control device it is established that a corresponding signal is output only when a particular adjustment angle is reached. In this way, direct angular adjustment for the foot part is carried out automatically and reproducibly.

The receiver or detector is coupled to the sensor device and/or to the signal generating element, in order to be able to carry out the above-described automatic matching either of the signal or of the signal triggering.

The signal generating element may likewise be coupled to a transmitter, so that the detected signal of the sensor does not need to be output directly at the prosthetic device, but may also be transmitted to a remotely arranged device. For example, signal transmission may be carried out to a cellphone, a tablet, a computer or another output device, so that besides the signal output or display, which with cellphones may be carried out both optically and acoustically and/or in a tactile fashion, storage of the values and shoes or height adjustments used can be carried out. The data available by means of this may be used to optimize the adjustment of the prosthetic set-up.

The adjustment device may comprise a shaft which is mounted eccentrically on the foot part, and is in turn mounted on the connection means. This straightforwardly provides the possibility, of carrying out adjustment of the proximal connection means relative to the foot part by rotating the eccentric shaft. Alternative configurations of the adjustment devices, for example by means of threaded rods, latching devices, or other form-fit locking means, are likewise possible and provided. The configuration using an eccentric shaft allows a spatially small configuration with sufficiently fine adjustment and secure latching. The eccentric shaft may be mounted in a yoke, on which the connection means is also mounted tiltably, so that there is the possibility of configuring the eccentric shaft essentially parallel to the tilt axis and the bearing axis of the connection means. In order to compensate for the longitudinal displacement of the eccentric shaft which occurs during rotation, the shaft is advantageously guided in a longitudinal hole guide in the connection means. The longitudinal hole may pass through the connection means. Of course it is possible and provided, that the eccentric shaft is mounted on the connection means, which is coupled to the connection means. It may also be that the longitudinal hole guide is formed not in the connection means but in the foot part. The adjustment device is therefore coupled to the connection means by means of an eccentrically mounted shaft, the shaft preferably being guided in a longitudinal hole guide.

The connection means may comprise a deactivatable blocking device, which blocks rotation of the foot part relative to the connection means, so that the orientation of the foot part relative to the connection means, once found, is maintained. The blocking device advantageously comprises retractable form-fit elements, so that activation or deactivation is straightforwardly possible.

The signal generating element is preferably configured as an active signal generating element, in order to deliver a clear signal, which is easy to pick up, about the adjusted heel height to the user.

The system consisting of a prosthetic foot as described above with a shoe provides the shoe with a readable heel height marking, so that, either optically, optoelectronically or electronically, the respectively existing heel height level can be read out and transmitted to the control device, to the position sensor or to the signal generating element, and a corresponding signal can subsequently be output when the correct heel height adjustment is reached. The heel height marking may be stored in an RFID chip, a transponder, or an optically or optoelectronically readable code. The heel height marking may also be applied to the shoe by bonding, embossing, embedding or in another way.

According to the method according to the invention for adapting the heel height of a prosthetic foot as described above to a shoe, which is assigned a heel height marking, the heel height marking is transmitted to a control device, the respective mark is compared with detected position data of the position sensor, and a confirmation signal is emitted when the position signal assigned beforehand to the respective heel height marking matches with the detected position signal. The heel height marking may be detected proximity-dependently by a detector, and the corresponding signal may be transmitted to the control device, for example when a detector or a transmitter enters into sufficient proximity or direct contact with the heel height marking. It is also possible to read out a corresponding code by means of optical detectors, for example scanners, and transmit it to the control device so that, after readout and processing of the corresponding code, a corresponding signal assignment and signal output are carried out.

Besides automatic detection and readout of the heel height marking and automatic transmission to the control device, it is in principle also possible to communicate the respective heel height manually to the control device for example by keying, remote control or latching or confirmation of a particular latch position.

In one variant of the invention, the prosthetic foot is assigned a drive so that the connection means is displaced in a motorized fashion relative to the foot part, the displacement being carried out as a function of the detected heel height so that automatic adaptation of the position of the foot part relative to the connection means is always carried out when putting on a shoe with a corresponding heel height marking.

BRIEF DESCRIPTION OF THE DRAWINGS

Exemplary embodiments of the invention will be explained in detail below with the aid of the figures, in which:

FIG. 12 shows a flow diagram of a method for adapting a heel height of a prosthetic foot to a shoe.

DETAILED DESCRIPTION

Figure 1:
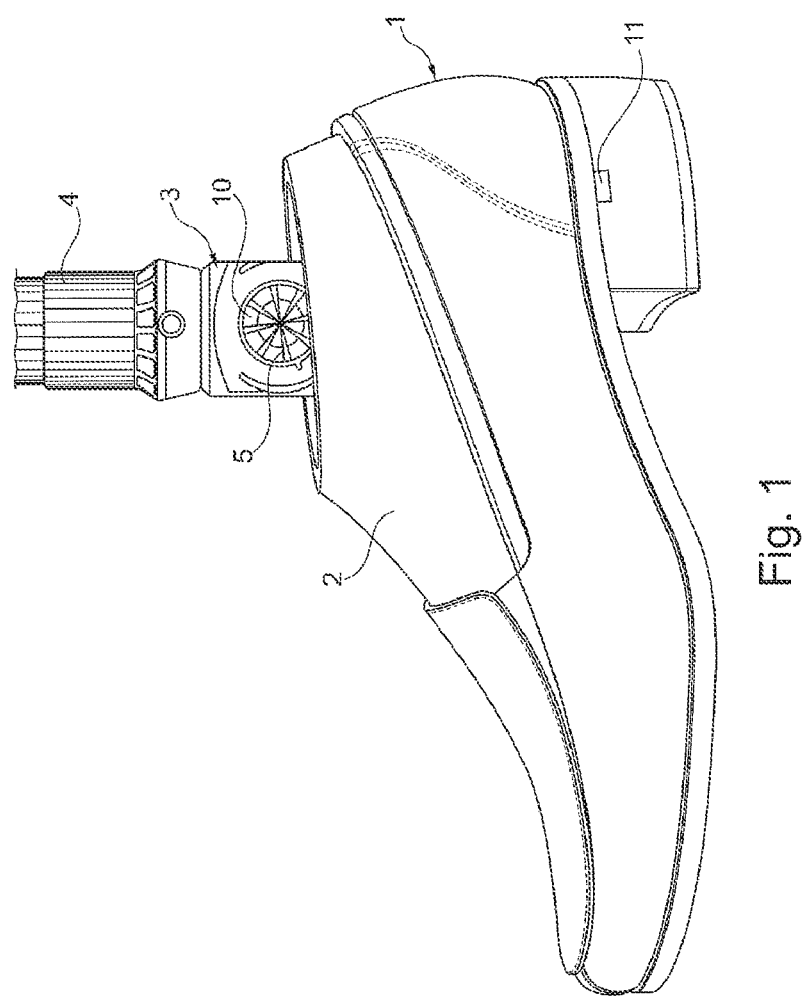
FIG. 1 shows a prosthetic foot in a shoe.

FIG. 1 shows a shoe 1 with, contained therein, a prosthetic foot which comprises a foot part 2 and proximal connection means 3 for connection to a lower limb tube 4. The proximal connection means 3 are mounted on the foot part 2 so that they can be tilted and comprise an adjustment apparatus device 5 by means of which the inclination of the foot part 2 relative to the connection means 3, or to the lower limb tube 4, can be adjusted. By means of the inclination adjustment of the foot part 2, it is possible to compensate for the different heel heights when changing shoes. A heel height marking 11 is arranged in the shoe 1, in the exemplary embodiment represented in the region of the heel, by means of which marking it is possible to identify the respective heel height and transmit it either manually or automatically to the adjustment device 5, or to a control device (not represented in FIG. 1), a signal generating element 10 or a sensor device. A signal generating element in the form of an output device for acoustic, tactile and/or optical signals, by means of which the prosthesis user can be informed about the respective setting of the heel height, is arranged on the adjustment device 5.

Figure 2:
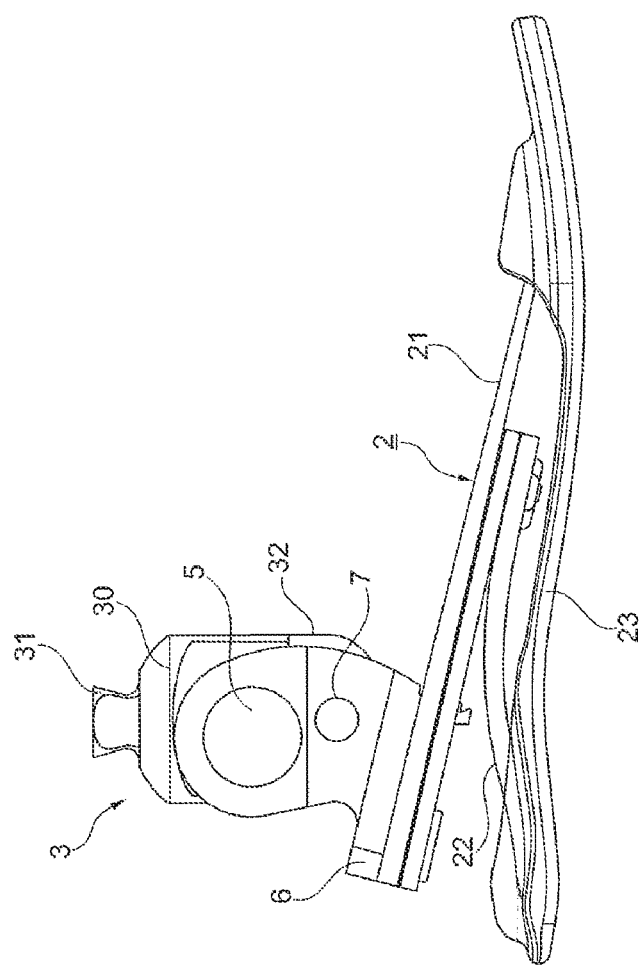
FIG. 2 shows a prosthetic foot insert in side view.

FIG. 2 shows a prosthetic foot insert without foot cosmetics with a foot part 2, which comprises a front-foot spring 21, a heel spring 22 and a base spring 23. Arranged at the rear end of the front-foot spring 21, there is a yoke 6 which extends in the proximal direction and is used to receive the proximal connection means 3. The yoke 6 is screwed firmly to the front-foot spring 21. The connection means 3 comprises a base body 30 with a pyramid adapter 31. A lower part 32 is fastened on the base body 30 and is used as a holder for a tilt axle 7, which passes transversely through the yoke 6. The connection means 3 is arranged between the two limbs of the yoke 6 and is mounted tiltably about the tilt axle 7. Furthermore, an adjustment device 5, the set-up of which is explained below, is mounted proximally with respect to the tilt axle 7 in the yoke 6. By means of the adjustment device 5, it is possible to modify the angular position of the foot part 2 relative to the connection means 3. By different inclinations of the connection means 3 relative to the foot part 2, it is possible to compensate for different heel heights of shoes (not represented).

Figure 3:
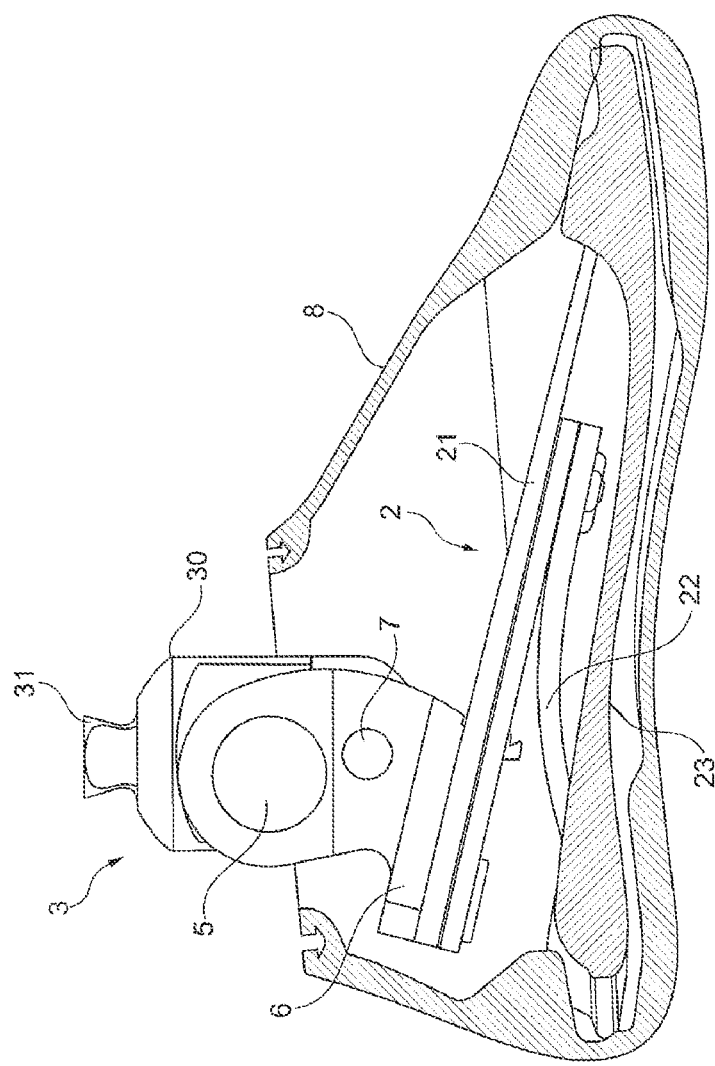
FIG. 3 shows a prosthetic foot insert according to FIG. 2 with foot cosmetics.

FIG. 3 shows the prosthetic foot insert according to FIG. 2 with foot cosmetics 8, into which the prosthetic foot insert is fitted together with the yoke 6 and parts of the connection means 3. The prosthetic foot insert together with the foot cosmetics form the prosthetic foot, which is fitted into a shoe. The foot cosmetics 8 form the distal extremity of the prosthetic foot and, because of the resilient properties, contribute to the functional behavior of the prosthetic foot. In the exemplary embodiment represented, the alignment of the connection means 3 relative to the foot part 2 is selected in such a way that there is a relatively shallow heel height, the sole or lower side of the foot cosmetics 3 being at on almost horizontal level at their bearing points.

Figure 4:
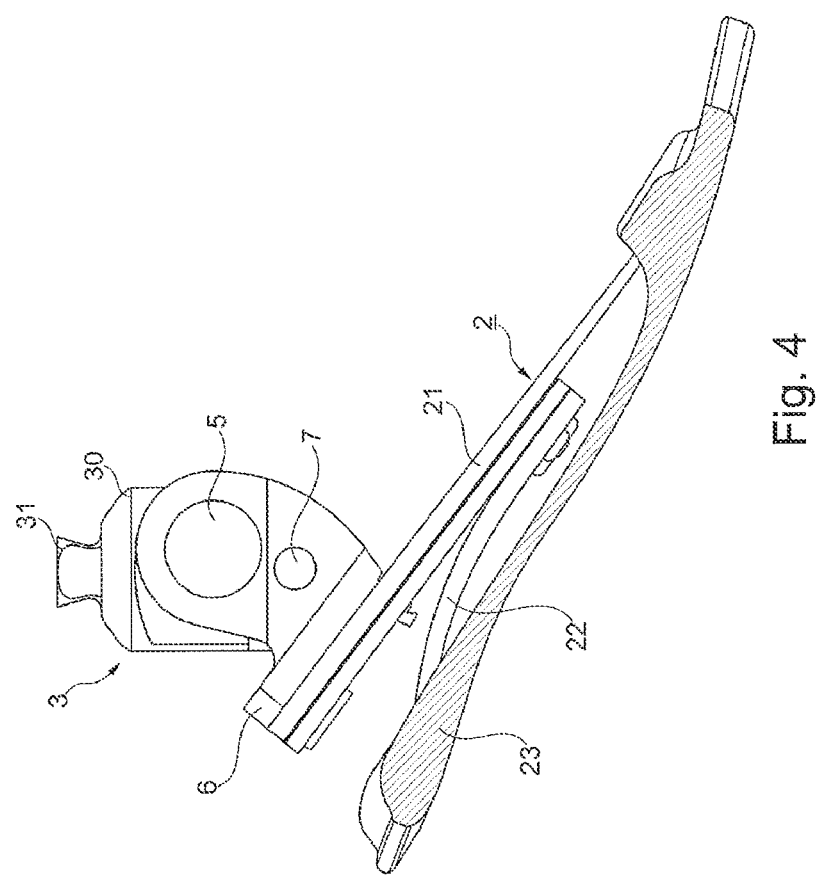
FIG. 4 shows an adjusted prosthetic foot insert.

FIG. 4 shows a variant of FIG. 2 in a maximally angled position, that is to say the foot part 2 has maximum plantar flexion and the connection means 3 have been rotated maximally about the tilt axle 7 counterclockwise relative to the yoke 6. The tip of the foot is substantially lower than the heel. Such a foot position is necessary when a shoe with a high heel is being worn on the other side, i.e. the untreated side, of the patient. If the foot position according to FIG. 2 was used with an increased heel height, this would lead to an unmanageable rolling behavior and a very unphysiological gait.

Figure 5:
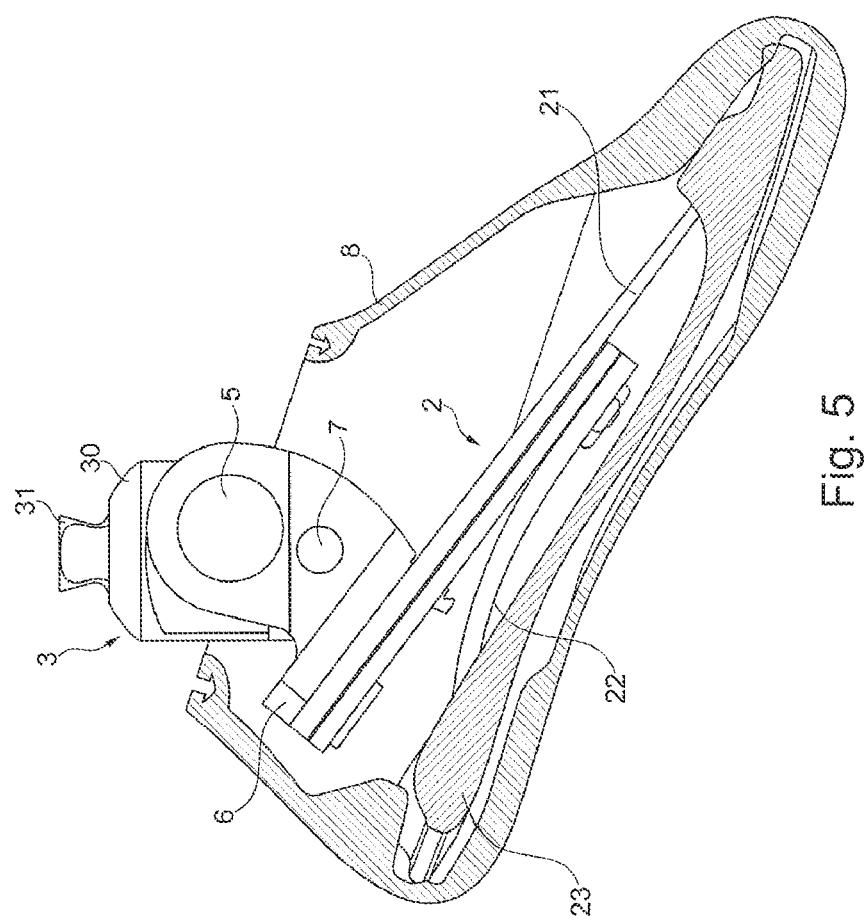
FIG. 5 shows a prosthetic foot insert according to FIG. 4 with foot cosmetics.

FIG. 5 shows the position of the foot according to FIG. 4 with foot cosmetics.

In order to be able to use foot positions according to FIGS. 3 and 5 together with a prosthetic set-up adjusted by an orthopedic technician, it is necessary to make the heel height adjustable. To this end, an adjustment device 5 is provided in the region of the connection means 3 on the bearing.

Figure 6:
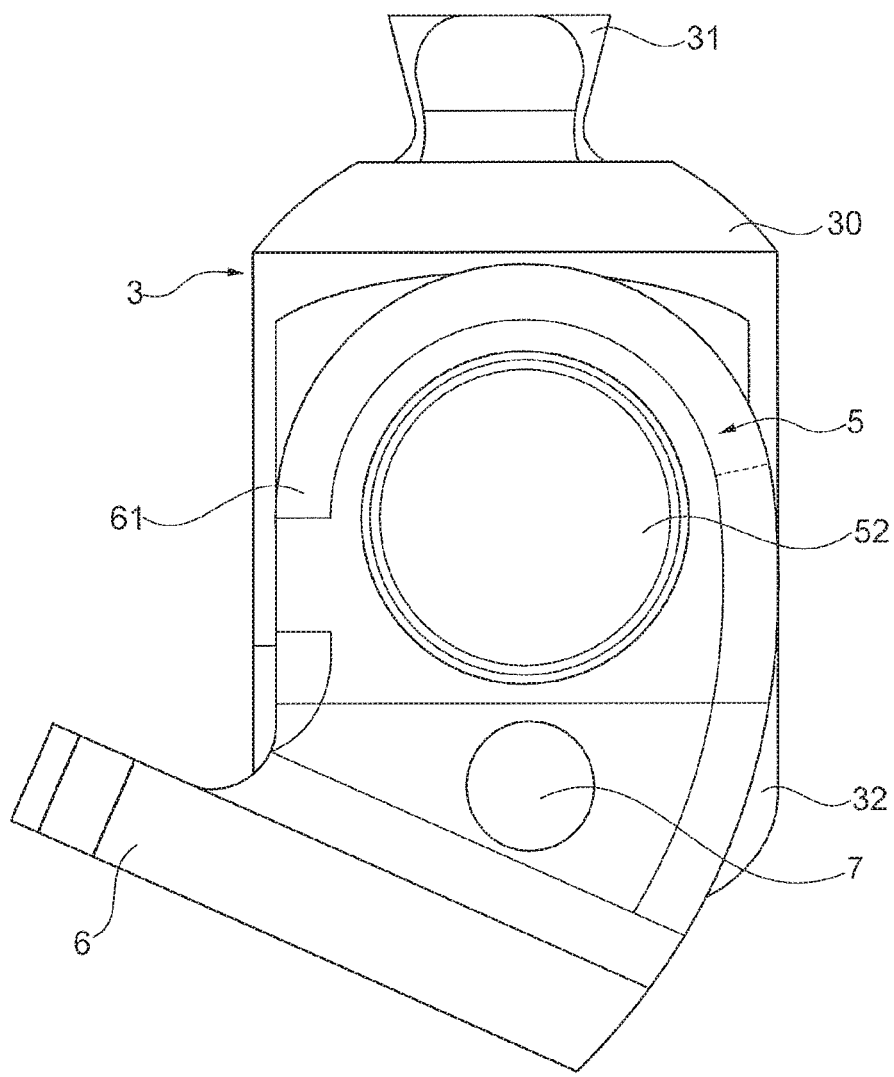
FIG. 6 shows a yoke with connection means in side view.

FIG. 6 shows the connection of the upper connection means 3 to the pyramid adapter 3, the base body 30 and the lower part 32 on the yoke 6 in a single representation. The proximal tilt axle 7 can likewise be seen as well as the adjustment device 5 arranged distally with respect thereto. FIG. 6 shows a side view of a carrier 61 or yoke limb with a circular recess, in which a bearing disk 52 is mounted. The functionality of the bearing disk 52 and of the adjustment device 5 will be explained below.

Figure 7:
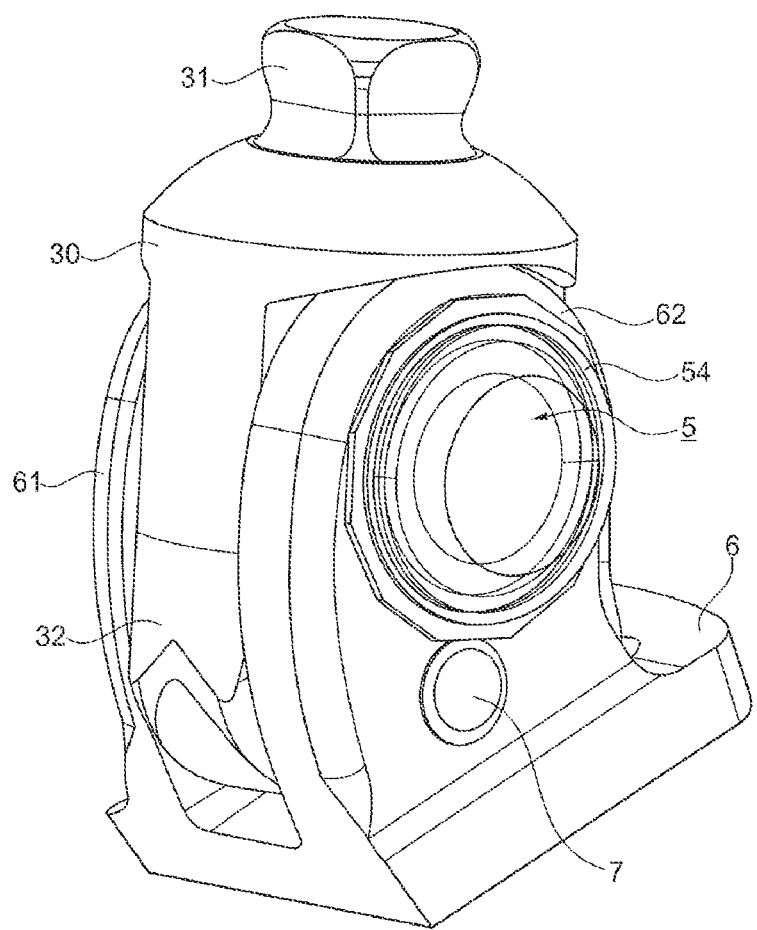
FIG. 7 shows FIG. 6 in perspective view.

FIG. 7 shows the arrangement according to FIG. 6 in a perspective view. It can be seen that the lower part 3 is fastened on the base body 30, and both the base body 30 and the lower part are arranged between two carriers 61, 62 or yoke limbs of the yoke 6. The adjustment device 5 has a cover cap 54 on the side of the second carrier 62 in order to protect various components of the adjustment device 5. In the exemplary embodiment represented, the connection means 3 is configured as a base body 30 with a pyramid adapter 31 fastened directly thereon. Besides such a configuration, it is also possible to provide an adapter between the pyramid adapter 31 and the yoke 6 or the foot part 2, for example in order to carry out a simpler length adjustment or alternatively in order to accommodate components of the adjustment device 5 in the adapter. For instance, an output device, a control device, and an input device for the programming of the respective heel height and the assignment to a signal, may be fitted in the adapter. The adjustment itself may also be carried out in the adapter, so that the pyramid adapter 31 does not necessarily need to be arranged, formed or fastened directly on the base body 30 of the adjustment device 5. The pyramid adapter 31 may also be fastened by means of an interposed intermediate piece or an adapter either to the base body 30 or in another way tiltably to the foot part 2, for example by means of a yoke 6 or another type of tiltable fastening on the foot part 2. Besides arrangement of the upper connection means 3 between the two carriers 61, 62 in the yoke, it is also possible to arrange the base body 30 only on one side on a single carrier, or alternatively to grip a central carrier on both sides by components of the upper connection means 3, so that the reverse arrangement compared with the exemplary embodiment represented is achieved.

Figure 8:
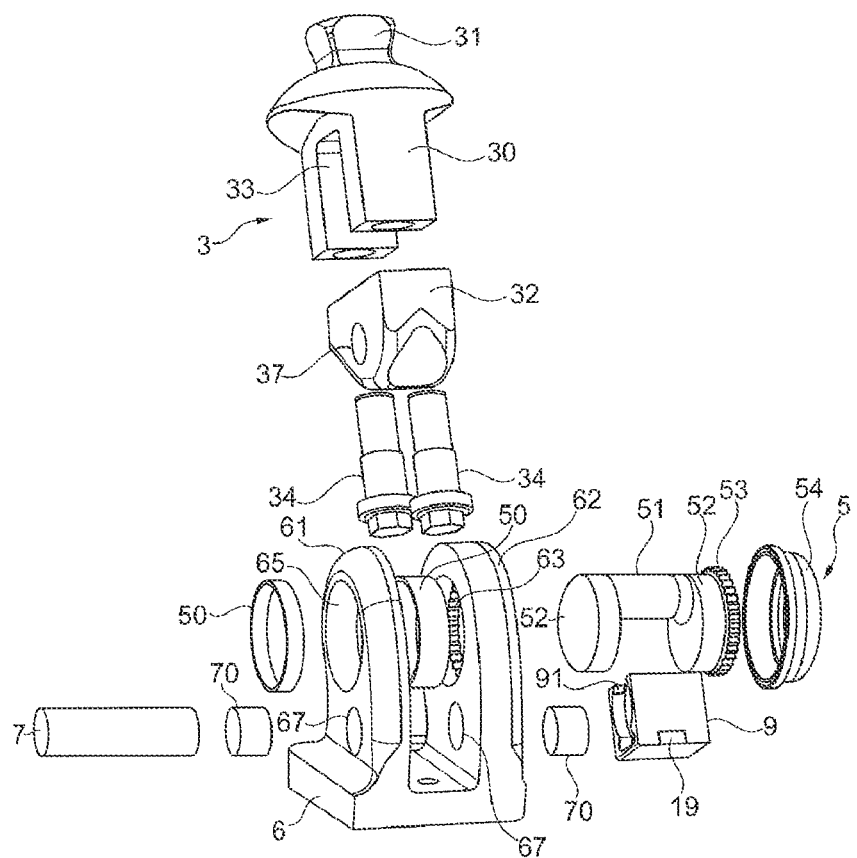
FIG. 8 shows an exploded representation of the adjustment device.

FIG. 8 shows, in an exploded representation, yoke 6 with through-bores 67 in the distal region of the carriers 61, 62 for receiving the tilt axle 7. The tilt axle 7 is mounted in bearings 70, which are formed as sliding bearings, in the through-bores 70. In the mounted state, the tilt axle 7 passes through both the carriers 61, 62 and the through-bore 37 inside the lower part 32, so that the lower part 32, which is screwed to the base body 30 by means of bolts 34, is mounted tiltably on the yoke 6. The tilt axle 7 in this case represents the rotation axis.

Above the through-bores 67, i.e. in the proximal direction, further bearing bores 65 are introduced, in which inner teeth 63 are formed in the right-hand carrier 62 on the outer side. Inside the bearing bores 65, bearing rings 50, which are likewise configured as sliding bearings, are arranged and accommodate bearing disks 52 of an eccentrically mounted shaft 51. The shaft 51 is guided in a longitudinal hole guide 33, which is configured as a through-slot, in the base body 30 and, in the event of rotation inside the bearing disks 50, causes tilting of the connection means 3 about the tilt axle 7. If the shaft 51 is rotated for example from a starting position in the direction of the rear end of the prosthetic foot, the connection means 3 are tilted relatively backward so that plantar flexion of the foot part 2 takes place, while if the shaft 51 is rotated in the direction of the tip of the foot, this causes dorsal flexion, that is to say the tip of the foot is raised in the direction of the prosthetic knee joint.

On the right-hand bearing disk 52 in the exemplary embodiment, outer teeth 53 are formed, which are produced in a manner corresponding to the inner teeth 63 on the carrier 62, so that when the teeth 53, 63 engage in one another rotation of the bearing disks 52 in the bearing bores 65 is blocked. The shaft 51 therefore cannot be moved and the connection means 3 is fixed in the adjusted position. In order to release the latching, or the blocking device which is formed by the teeth 53, 63, the left-hand bearing disk 52 is pressed on so that both the shaft 51 and the right-hand bearing disk 52 are displaced in the direction of the cover cap 54. In this way, the outer teeth 53, which act as form-fit elements in the inner teeth 63, are disengaged and retracted so that free rotatability of the bearing disks 52 inside the bearing bores 65 can be carried out.

FIG. 8 likewise shows a position sensor 9, which detects the position of the foot part 2, which is connected firmly to the yoke 6 by screwing, relative to the connection means 3. The position sensor 9 may be configured either as a location sensor, which detects the orientation of the foot part in space during an adjustment mode, or as a relative sensor which, starting from an initial position, detects the relative position of the foot part 2 via the position of the yoke 6 relative to the connection means 3.

Also mounted on the sensor 9, there is an adjustable transmitter 91 by means of which it is possible to adjust when a position signal of the sensor 9 is output, in order to carry out preselection of the signals to be output.

The sensor 9 is advantageously configured as a Hall sensor, in which either a magnet is displaced relative to a multiplicity of coils or many magnets are displaced relative to a coil because of the rotation of the shaft 51 or of the bearing disks 52 relative to the sensor 9. A signal is generated because of the Hall effect, which is evaluated and on the basis of which signal output is carried out by the output device 10.

Figure 9:
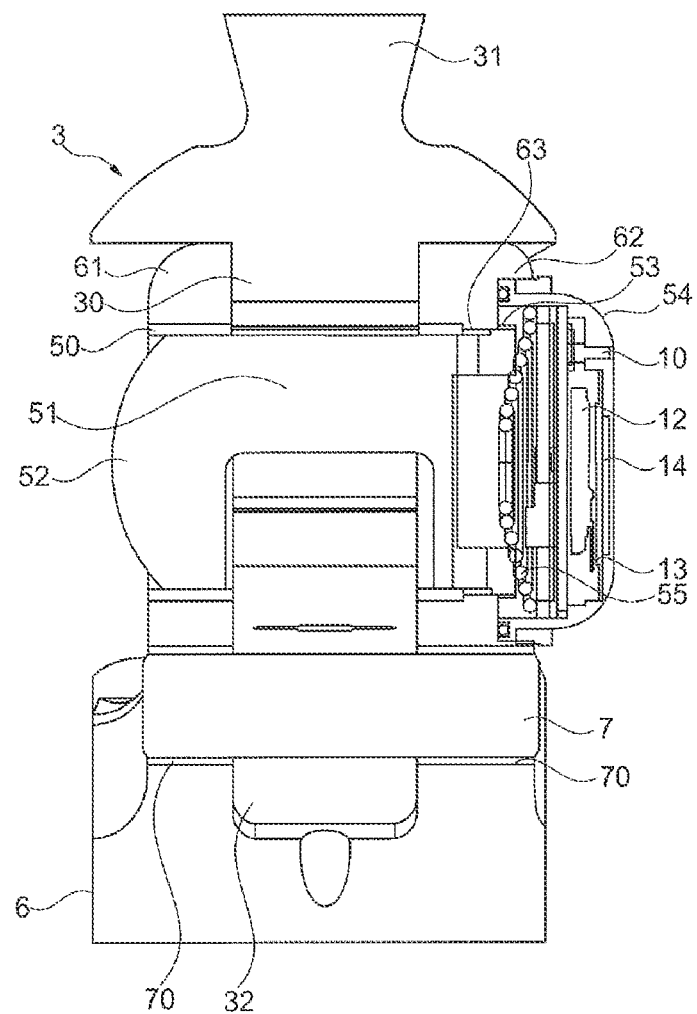
FIG. 9 shows a sectional representation of the adjustment device.

FIG. 9 shows a sectional representation of an embodiment which essentially corresponds to that of FIG. 8. The position sensor is not represented. In FIG. 9, the connection means 3 is shown in a latched state. The yoke 6 with the two carriers 61, 62 essentially aligned parallel to one another receives the connection means 3 and in particular the base body 30 and the lower part 32 between the two carriers 61, 62. The tilt axle 7 is mounted on the yoke 6 in such a way that it can be tilted by means of the bearing 70. The eccentric shaft 51 is mounted inside the longitudinal hole guide in the base body 30. The two bearing disks 52 are mounted rotatably in bearing shells 50 in the bearing bores 65. The outer teeth 53 on the right-hand bearing disk 52 engage in the inner teeth 63 on the right-hand carrier 62, and therefore block tilting of the connection means 3 about the tilt axle 7.

Mounted inside the cover cap 54, there is a compression spring 55 which presses the bearing disk 52 with the outer teeth 53 in the direction of the inner teeth 63. In this way, form-fit latching of the shaft 51 relative to the yoke 6 is ensured. In order to unblock the latching, a pressure force is applied onto the bearing disk 52 on the side facing away from the cover cap 54, so that the shaft 51 is displaced to the right and the teeth 53, 63 are disengaged.

Arranged inside the cover cap 54, there is a control device 12 which, on the basis of the received position signal of the position sensor 9, activates an output device 10 for an optical and/or acoustic and/or haptic signal. The output device 10 may for example indicate a heel height level by a rhythmical signal, although it is likewise possible to provide voice output or to report that a preadjusted setpoint position has been reached by means of a confirmation signal. The setpoint position may be established by the control device 12, for example by a detector 19, for example an RFID receiver, receiving a signal of a heel height marking 11 and establishing a corresponding angular position of the foot part 2 relative to the connection means 3 as a setpoint position. If this setpoint position is reached during the adjustment of the foot part 2 relative to the connection means 3, a confirmation signal is sounded or a different confirmation signal is output. It is also possible for the heel height marking to be transmitted to the control device 12 in a different way, for example manually by rotation of a setting device, by repeated pressing or actuation of a switch, in order to input the corresponding heel height level, by voice input, by a remote control or in another way. Certain switches or microswitches may also be activated manually so that, when there is a corresponding angular position, a confirmation signal is output or a warning signal, which indicates an incorrect heel height adjustment, is interrupted.

The control device 12 is assigned a transmitter 13, by means of which it is possible to transmit the signals of the sensor 9 (not represented) to a remote output device 10, for example a cellphone, a computer or the like. The control device 12 is furthermore assigned a confirmation device 14, which in the exemplary embodiment represented is configured as a confirmation button in the cover cap 54. The confirmation button 14 is used to carry out confirmation during the assignment of the respective heel height to the signal. If the heel height is for example adjusted chronologically, the first heel height adjusted is assigned a first signal by confirming the adjusted heel height by means of the confirmation button of the control device 12. The control device 12 assigns a first signal to this heel height. When a second heel height is adjusted and the confirmation button 14 is actuated again, the second output signal is assigned to this heel height, regardless of whether the second heel height is greater or less than the first heel height. If a heel height adjustment is deleted, this is made free and can be respecified, and here again it is not essential to store or arrange the heel heights in a particular order. After the adjustment and confirmation of the respective heel height and the assignment of the respective signal the prosthetic foot can be used. If a shoe is changed the heel height is adjusted by actuating the adjustment device 5. To this end, the teeth 53, 63 are disengaged by displacement against the pressure force of the error 55, and the foot part 2 is tilted relative to the connection means 3 until a signal is output. The signal may be output to the user by means of the output device 10 in the form of a light signal and by means of an acoustic signal transmitter. When the desired position of the foot part relative to the connection means 3 is reached, the teeth 53, 63 are latched. If latching has been carried out, it is possible to output an additional signal which signals that the prosthetic foot is ready to be used.

Besides the active signal output described, it is possible not to provide an energy source for the signal output, but rather to induce the signal output by the adjustment itself. To this end, so-called chatter marks may be used, which output the adjustment of the foot part 2 relative to the upper connection means 3 in a tactile fashion and acoustically. In addition to the latching, it is possible for an acoustic output element to be provided, which for example emits an acoustic signal by a spring flipping over when a heel height level is reached or exceeded. In addition, an optical display may be assigned to the adjustment.

With the prosthetic foot, it is possible to provide an adjustment aid for the prosthetic foot in order to adapt different heel heights reproducibly with an overall prosthetic set-up which has been adjusted by an orthopedic technician. By means of the control device 12, it is possible to select particular heel height levels beforehand, so that, for example, after reviewing the shoes available with different heel heights, fitting is carried out by the orthopedic technician. If four different heel heights are available, for example, the optimal angular position of the foot part 2 relative to the connection means 3 may be programmed in for each heel height. The programming into the control device 12 may be carried out manually by means of push-buttons, by means of rotary switches or alternatively by means of a wireless connection. In this way, filtering of the multiplicity of possible heel height adjustments down to remaining adjustments which are relevant to the patient is carried out by the orthopedic technician. The signal output for the heel height to be adjusted is then carried out in a manner adapted to the patient, so that only the four selected heel heights are still available for selection and not all heel height levels, which may be graduated very finely, have to be included or perceived. The signaling of the relevant heel height adjustments is thus carried out according to a preselection by the orthopedic technician, so that the patient is not irritated by irrelevant position signals. It is also possible for the positions selected by the orthopedic technician be provided with a different signal than the other latching positions, for example by a difference in tone, volume, light color or the like.

The heel height marking 11 may also be input by means of a voice command, so that a particular shoe with a corresponding marking is announced to the prosthetic foot and the respectively assigned heel height is provided with a corresponding signal by means of voice recognition.

Figure 10:
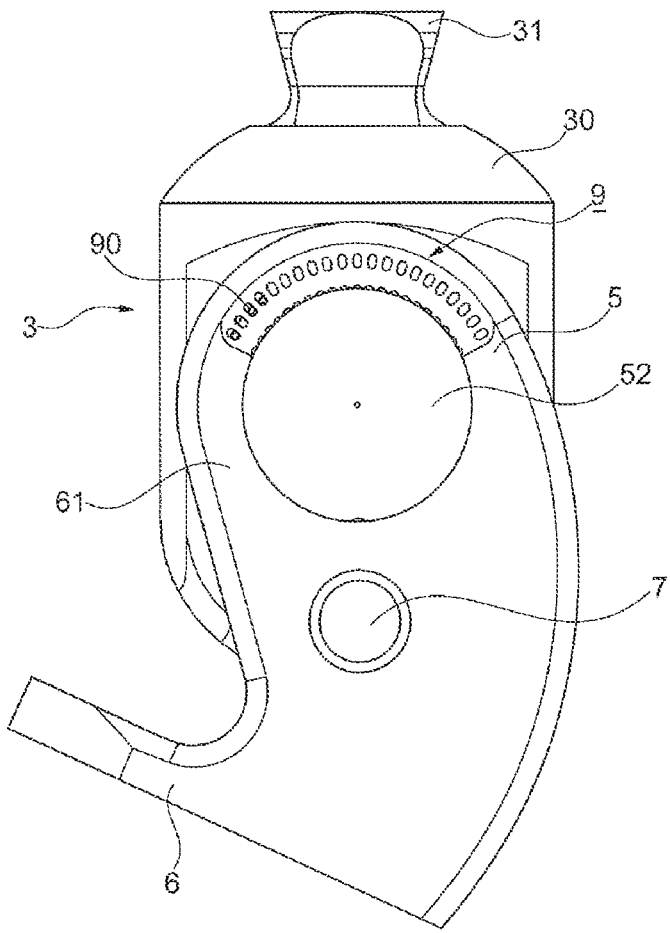
FIG. 10 shows a variant of the invention in side view.

FIG. 10 shows a side view of a variant of the invention, which corresponds in its basic set-up to that of FIG. 6. In the exemplary embodiment represented, the position sensor 9 is configured as a mechanical sensor, integrated in which there are so-called dip switches 90 that extend over a circular arc along a tilting path of the proximal connection means 3 relative to the yoke 6. By displacement of the dip switches 90, latching devices are blocked or released, contacts are blocked or released, or both are carried out, so that the reaching of a particular position of the base body 30 relative to the yoke 6 or the adjustment device 5 is displayed, felt or heard and/or can be displayed or output. In the exemplary embodiment represented, different positions of the respective dip switch 90 are shown in the recesses on the left.

Figure 11:
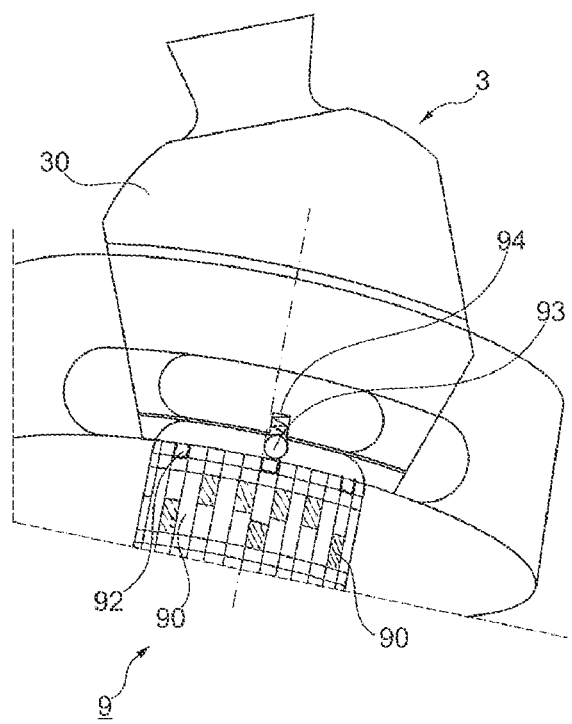
FIG. 11 shows a detailed view of a position sensor.

FIG. 11 shows a schematic representation of the functionality and of the set-up of the mechanical position sensor arrangement according to FIG. 10 in a sectional representation. The proximal connection means 3 with the base body 30 is in turn mounted on the yoke so that it can be tilted about the tilt axle 7 (not represented). The dip switches 90 of the mechanical position sensor 9 are arranged in the shape of a fan at uniform intervals from one another, a total of ten dip switches 90 being provided in the exemplary embodiment represented. The two respective outer dip switches 90 and the central dip switch 90 are arranged in a retracted release position oriented in the direction of the tilt axle 6, and the others are oriented in a blocking position. In the release position, latching recesses 92 in which a latching element 93 in the shape of a ball can latch are released by the dip switches 90. The ball 93 is prestressed in the direction of the latching recesses 92 by a spring 94, so that during adjustment of the connection means 3 the ball 93 latches in the respectively released latching recess 92. By the uniform fan-shaped arrangement of the dip switches 90, display is possible in an acoustic and tactile fashion over the entire tilting path of the connection means 3 at uniform angular intervals. The two respective outer dip switches 90 and the associated latching recesses 92 represent the endpoints of the tiltability. In the embodiment represented, the proximal connection means 3 is positioned in a central position, out of which tilting may be carried out in the respective tilting direction, where appropriate after unlatching.

By the latching of the ball 93 into the latching recess 92, it is also possible to close an electronic contact so that a signal relating to the reaching of a particular angular position can be output electronically, for example by means of a computer, a cellphone or a display device specially equipped therefor. By the contact, it is also possible to output an acoustic signal that goes beyond the mechanical latching noise of the ball 93 in the latching recess 92 and is generated separately, for example by means of a signal generator in the form of a loudspeaker or another sound generating device, which is activated when the contact is closed and actively generates a signal which differs from the latching noise.

When the dip switches 90 are closed, the ball 93 rolls over the surface of the dip switches which are closing the latching recesses 92 in the locking position, so that no haptic and/or acoustic messaging to the user takes place. Besides a uniformly separated arrangement of the dip switches 90 next to one another, it is also possible to arrange them at nonuniform intervals from one another in order to allow precise adjustability at preferred positions, so that intermediate positions can also be occupied.

Besides the arrangement of the dip switches 90 only on the upper half around the bearing disk 51, as shown in FIG. 10, it is also possible to arrange dip switches additionally on the opposite lower side, the dip switches on the lower side being offset by half the interval, so that halved gradation of the angular adjustability is possible. In this way, it is possible to achieve finer adjustabilities, with at the same time a sufficient size of the dip switches 90 so that handleability of the dip switches 90 is still ensured. The dip switches may be configured as slide switches which are mounted longitudinally displaceably in guides. By the configuration of the form-fit element 93 as a ball, it switches possible to allow rolling over the surface of the dip switches in the closed position against a certain resistance by the spring 94 and to move the ball 93 out of the recess 92.

The invention claimed is:

1. A method for adapting a heel height of a prosthetic foot to a shoe, the prosthetic foot comprising a foot part, a proximal connection member pivotally connected to the foot part, an output device, a control device, and at least one position sensor, the method comprising:
assigning a heel height marking to the shoe, the heel height marking representing a value of a heel height of the shoe;
assigning a position signal to the heel height marking;
transmitting the value of the heel height of the shoe to the control device;
adjusting the heel height of the prosthetic foot at least partially based on the heel height marking;
comparing, with the control device, the value of the heel height marking with detected position data from the at least one position sensor; and
emitting a confirmation signal with the output device when the position signal assigned to the heel height marking matches with the detected position data, wherein the confirmation signal is an acoustic signal, the acoustic signal including at least one of different pitch levels, signal patterns, or signal sequences assigned to specific heel height levels of the foot part.

2. The method as claimed in claim 1, further comprising:
automatically reading the heel height marking with the at least one position sensor; and
transmitting the value of the heel height marking to the control device.

3. The method as claimed in claim 1, wherein the prosthetic foot further comprises an adjustment device, the method further comprising:
displacing, with the adjustment device, the connection member relative to the foot part,
the adjustment device being operable without the use of a motor.

4. A method for adjusting a heel height of a prosthetic foot to a shoe, the prosthetic foot comprising a foot part and a proximal connection member pivotally connected to the foot part, an output device, and an adjustment device, the adjustment device including at least one position sensor and being operable to adjust a position of the foot part relative to the proximal connection member, the method comprising:
detecting a position of the foot part relative to the proximal connection member;
generating an output with the output device as a function of the detected position, the output informing a user of the prosthetic foot about a position of the foot part relative to the proximal connection member, wherein the output is an acoustic signal, the acoustic signal generated by a voice generating device and including an announcement about a heel height level of the foot part.

5. The method as claimed in claim 4, wherein the output device is configured to generate at least one of optical, tactile and acoustic outputs.

6. The method as claimed in claim 4, wherein the adjustment device comprises latch elements operable to provide adjustment of the foot part relative to the connection member in discrete steps.

7. The method as claimed in claim 4, wherein the at least one position sensor is configured as at least one of a location sensor, a relative angle sensor, an inertial angle sensor or a switch.

8. The method as claimed in claim 4, wherein the at least one position sensor comprises an adjustable or programmable signal generator.

9. The method as claimed in claim 4, wherein the adjustment device is operable without the use of a motor.

10. The method as claimed in claim 4, wherein the output includes a confirmation that the foot part has reached a setpoint position, the setpoint position being a heel height.

11. The method as claimed in claim 4, wherein the output is a tactile signal vibration, the tactile signal vibration including a pattern associated with heel height levels of the foot part.

12. The method as claimed in claim 4, wherein the output is an optical signal, the optical signal including at least one of a light signal, a light signal pattern, or information presented on a display.

13. The method as claimed in claim 5, wherein one or more of the optical, tactile and acoustic outputs are provided individually or in combination with each other.

14. The method as claimed in claim 4, wherein the output includes different types of output for different heel height levels.

15. The method as claimed in claim 4, wherein the output is an optical signal, the optical signal including different colors for different heel height levels.

16. A method for adjusting a heel height of a prosthetic foot to a shoe, the prosthetic foot comprising a foot part, a proximal connection member connected to the foot part, an output device, and an adjustment device to adjust the foot part relative to the connection member without the use of a motor, the adjustment device including at least one position sensor, the at least one position sensor being coupled to the output device, the method comprising:
detecting, with the at least one sensor, an adjusted position of the foot part relative to the proximal connection member;
generating a position signal;
communicating, with the output device, an acoustic output to a user confirming, based on the position signal, that a setpoint position for the foot part has been reached, wherein the setpoint position is at least partially determined by a heel height of the shoe, wherein the acoustic signal includes a different tone for each heel height level of the foot part.

17. A method for adapting a heel height of a prosthetic foot to a shoe, the shoe comprising a heel height marking representing a heel height of the shoe, the prosthetic foot comprising a foot part, a proximal connection member pivotally connected to the foot part, an output device, a control device, and at least one position sensor, the method comprising:

receiving a value of the heel height marking, the heel height marking representing a value of a heel height of the shoe;

assigning a position signal to the heel height marking;

transmitting the value of the heel height of the shoe to the control device;

adjusting the heel height at least partially based on the heel height marking;

comparing, with the control device, the value of the heel height marking with detected position data from the at least one position sensor; and emitting a confirmation signal with the output device when the position signal assigned to the heel height marking matches with the detected position data.

18. A method for adapting a heel height of a prosthetic foot to a shoe, the shoe comprising a heel height marking representing a heel height of the shoe, the prosthetic foot comprising a foot part, a proximal connection member pivotally connected to the foot part, an output device, a control device, and at least one position sensor, the method comprising:

transmitting a value of the heel height marking from the shoe, the heel height marking representing a value of a heel height of the shoe;

receiving, by the control device, the heel height marking;

assigning a position signal to the heel height marking;

transmitting the value of the heel height of the shoe to the control device;

adjusting the heel height at least partially based on the heel height marking;

comparing, with the control device, the value of the heel height marking with detected position data from the at least one position sensor; and emitting a confirmation signal with the output device when the position signal assigned to the heel height marking matches with the detected position data.

19. A method for adapting a heel height of a prosthetic foot to a shoe, the shoe comprising a heel height marking representing a heel height of the shoe, the prosthetic foot comprising a foot part, a proximal connection member pivotally connected to the foot part, an output device, a control device, and at least one position sensor, the method comprising:

transmitting a value of the heel height marking from the shoe, the heel height marking representing a value of a heel height of the shoe;

receiving, by the control device, the heel height marking;

assigning a position signal to the heel height marking;

transmitting the value of the heel height of the shoe to the control device;

adjusting the heel height at least partially based on the heel height marking;

automatically detecting, by the at least one position sensor, at least one detected position data;

automatically comparing, with the control device, the value of the heel height marking with the detected position data from the at least one position sensor; and emitting a confirmation signal with the output device when the position signal assigned to the heel height marking matches with the detected position data.

\* \* \* \* \*